(12) United States Patent
Azar et al.

(10) Patent No.: US 7,901,076 B2
(45) Date of Patent: *Mar. 8, 2011

(54) OCULAR WAVEFRONT-CORRECTION PROFILING

(75) Inventors: Dimitri T. Azar, Brookline, MA (US); Damien Gatinel, Paris (FR); Jacques Malet, Paris (FR)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/032,395

(22) Filed: Feb. 15, 2008

(65) Prior Publication Data
US 2008/0198331 A1    Aug. 21, 2008

Related U.S. Application Data

(63) Continuation of application No. 11/287,510, filed on Nov. 22, 2005, now Pat. No. 7,331,668, which is a continuation-in-part of application No. 10/894,255, filed on Jul. 19, 2004, now Pat. No. 7,341,345.

(51) Int. Cl.
*A61B 3/10* (2006.01)
*A61B 3/00* (2006.01)
(52) U.S. Cl. .......................... 351/205; 351/246
(58) Field of Classification Search .......... 351/200–221, 351/246
See application file for complete search history.

(56) References Cited

U.S. PATENT DOCUMENTS

| 4,525,043 | A | 6/1985 | Bronstein | 351/161 |
|---|---|---|---|---|
| 5,677,750 | A | 10/1997 | Qi | 351/205 |
| 5,755,664 | A | 5/1998 | Rubenstein | 600/377 |
| 6,059,775 | A | 5/2000 | Nielsen | 600/5 |
| 6,547,392 | B2 | 4/2003 | Fujieda | 351/212 |
| 6,663,619 | B2 | 12/2003 | Odrich et al. | 606/5 |
| 6,679,606 | B2 | 1/2004 | Campin et al. | 351/211 |
| 7,331,668 | B2 * | 2/2008 | Azar et al. | 351/205 |
| 7,341,345 | B2 * | 3/2008 | Azar et al. | 351/205 |
| 2003/0076478 | A1 | 4/2003 | Cox | 351/219 |
| 2003/0199858 | A1 * | 10/2003 | Schelonka | 606/5 |
| 2004/0169820 | A1 | 9/2004 | Dai et al. | 351/177 |
| 2005/0024585 | A1 | 2/2005 | Dai | 351/205 |
| 2005/0187622 | A1 | 8/2005 | Sandstedt et al. | 351/161 |
| 2005/0280777 | A1 | 12/2005 | Dai | 351/246 |
| 2006/0017883 | A1 | 1/2006 | Dai et al. | 351/246 |

FOREIGN PATENT DOCUMENTS

| EP | 1332712 | 8/2003 |
|---|---|---|
| WO | WO 02/064031 | 8/2002 |
| WO | WO 2004/053568 | 6/2004 |

OTHER PUBLICATIONS

Anschutz, T., "Laser Correction of Hyperopia and Presbyopia", Int. Ophthalmol. Clin., 34(4):107-37 (1994 Fall). cited by other.

(Continued)

*Primary Examiner* — Mohammed Hasan
(74) *Attorney, Agent, or Firm* — Fish & Richardson P.C.

(57) ABSTRACT

Providing multi-focal visual correction includes determining a plurality of visual conditions to which an eye is to be exposed, determining effects of the visual conditions on a pupil of the eye, and determining a target wavefront profile on the basis of the effects.

32 Claims, 12 Drawing Sheets

OTHER PUBLICATIONS

Bauerberg, J., "Centered vs. Inferior Off-center Ablation to Correct Hyperopia and Presbyopia", J. Refract. Surg., 15(1):66-9, (Jan.-Feb. 1999). cited by other.

Epstein et al., "Correction of Presbyopia with Excimer Laser", Int. Ophthalmol. Clin. 41(2):103-11 (2001 Spring). cited by other.

Vinciguerra et al., "Zonal Photorefractive Keratectomy for Presbyopia", J. Refract. Surg., 14(2 Suppl):S218-21, (Apr. 1998). cited by other.

Vinciguerra et al., "Excimer Laser Photorefractive Keratectomy for Presbyopia: 24-month Follow-up in Three Eyes", J. Refract. Surg., 14(1):31-7, (Jan.-Feb. 1998). cited by other.

Gatinel, D. et al. "Effects of the Pupil Constriction on the Wavefront Zernike Terms." Abstract only. *Invest Ophthalmol Vis Sci*, 2003, vol. 44, No. 5. 2 pages, June.

Guirao, Antonio et al. "Effect of rotation and translation on the expected benefit of an ideal method to correct the eye's higher-order aberrations." *Journal of Optical Society of America*, May 2001, vol. 18, No. 5. pp. 1003-1015.

Wyatt, Harry J. "The Form of the Human Pupil." *Vision Res.*, 1995, vol. 35, No. 14. pp. 2021-2036, May.

Walsh, G. et al. "The Effect of Pupil Centration and Diameter on Ocular Performance." *Vision Res.* vol. 28, No. 5, 1988, pp. 659-665, September.

Supplementary European Search Report in EP application No. 05773821.3, dated Aug. 27, 2009, 10 pages.

* cited by examiner

OCULAR WAVEFRONT-CORRECTION PROFILING

CROSS-REFERENCE TO RELATED APPLICATIONS

This application is a continuation of and claims priority to U.S. application Ser. No. 11/287,510, filed on Nov. 22, 2005 now U.S. Pat. No. 7,331,668, which is a continuation-in-part application of U.S. application Ser. No. 10/894,255, filed on Jul. 19, 2004 now U.S. Pat. No. 7,341,345, each of which is incorporated herein by reference.

FIELD OF INVENTION

The invention relates to ocular wavefront-correction profiling.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances is referred to as "accommodation."

As a person ages, the lens loses plasticity. As a result, it becomes increasingly difficult to deform the lens sufficiently to focus on objects at different distances. This condition is known as presbyopia. Refractive errors caused by such conditions as hyperopia, myopia, as well as aberrations due to irregularities in the eye (e.g., in the cornea or in the natural crystalline lens) can also degrade one's ability to focus on an object. To compensate for this loss of function, it is useful to provide different optical corrections for focusing on objects at different distances.

One approach to applying different optical corrections is to carry different pairs of glasses and to swap glasses as the need arises. For example, one might carry reading glasses for reading and a separate pair of distance glasses for driving.

In another approach, bifocal lenses assist accommodation by integrating two different optical corrections onto the same lens. The lower part of the lens is ground to provide a correction suitable for reading or other close-up work while the remainder of the lens is ground to provide a correction for distance vision. To regard an object, a wearer of a bifocal lens need only maneuver the head so that rays extending between the object-of-regard and the pupil pass through that portion of the bifocal lens having an optical correction appropriate for the range to that object.

Laser eye surgery techniques for improving focusing ability involve laser ablation of a portion of the eye. In Photorefractive Keratectomy (PRK) surgery, a surgeon uses an excimer laser to remove tissue from the surface of the cornea. In Laser-Assisted In Situ Keratomileusis (LASIK) surgery or Laser Epithelial Keratomileusis (LASEK) surgery, a surgeon removes tissue under the surface of the cornea by lifting a portion (a "flap") of the cornea. Tissue is selectively removed to reshape the cornea so that less deformation of the lens is necessary for accommodation. Customized laser eye surgery based on measurements of a subject's eye can also compensate for some wavefront aberrations. During laser eye surgery, the cornea is reshaped to improve vision for a single distance of regard. Vision at other distances may remain degraded. For example, even after laser eye surgery, a subject may still need to use glasses to correct far vision. It may be desirable to improve vision at more than one distance of regard.

SUMMARY

The invention is based, in part, on the recognition that including features in a wavefront-correction profile that are based on measurement of a pupil size and/or location can be used for providing multi-focal visual correction in an eye.

In one aspect, the invention features a method for providing multi-focal visual correction. The method includes determining a plurality of visual conditions to which an eye is to be exposed, determining effects of the visual conditions on a pupil of the eye, and determining a target wavefront profile on the basis of the effects.

In some embodiments, the method further includes determining a wavefront aberration map for the eye; and determining a wavefront-correction profile on the basis of the target wavefront profile and the wavefront aberration map.

In some embodiments, determining effects of the visual conditions on a pupil of the eye includes determining a change in a size of a pupil of the eye, or a change in a position of the pupil.

In some embodiments, determining effects of the visual conditions on a pupil of the eye includes estimating pupil conditions corresponding to each of the plurality of visual conditions.

In some embodiments, determining a plurality of visual conditions includes simulating a plurality of desired visual conditions; and determining effects of the visual conditions on a pupil of the eye includes measuring pupil conditions resulting from each of the desired visual conditions.

In some embodiments, determining effects of the visual conditions on a pupil of the eye includes determining a pupil condition corresponding to a lighting condition.

In some embodiments, determining the pupil condition further includes determining the pupil condition corresponding to a distance of regard.

In some embodiments, determining a target wavefront profile includes selecting a plurality of distances to objects of regard and determining the target wavefront profile at least in part on the basis of the plurality of distances.

In some embodiments, determining a plurality of visual conditions includes inferring desired visual conditions on the basis of measurements indicative of a subject's intent to accommodate for the desired visual conditions.

In some embodiments, the method further includes determining the wavefront-correction profile at least in part on the basis of a point spread function, an optical transfer function, a modular transfer function, or a phase transfer function.

In some embodiments, determining effects of the visual conditions on a pupil of the eye includes determining pupil conditions, and a pupil position corresponding to a first pupil condition is non-concentric with a pupil position corresponding to a second pupil condition.

In some embodiments, determining the target wavefront profile includes providing a first set of modified coefficients as a function of a set of target coefficients and a first pupil condition, providing a second set of modified coefficients as a function of the set of target coefficients and a second pupil condition, selecting the set of target coefficients according to constraints for at least one of the first set of modified coefficients and at least one of the second set of modified coefficients, and determining the target wavefront profile based on the target coefficients.

In some embodiments, the method further includes determining a wavefront aberration map for the eye, providing a set of reference coefficients of spatial modes corresponding to the wavefront aberration map, and determining a wavefront-correction profile based on the target coefficients and the reference coefficients.

In some embodiments, further includes performing laser ablation on the cornea of the eye according to the wavefront-correction profile.

In some embodiments, determining the wavefront-correction profile includes simulating an image based on a plurality of candidate wavefront-correction profiles for a subject, and selecting the wavefront-correction profile based on the feedback from the subject.

In another aspect, the invention features an optical element for placement in an eye. The optical element includes a surface that is shaped according to a wavefront-correction profile that includes features based on a target wavefront profile. The target wavefront profile includes features based on effects of a plurality of visual conditions on a pupil of the eye.

In some embodiments, the wavefront-correction profile includes features based on a difference between the target wavefront profile and a reference wavefront profile determined from the wavefront aberration map.

In some embodiments, the effects of the visual conditions on the pupil of the eye include a change in a size of a pupil of the eye, or a change in a position of the pupil.

In some embodiments, the optical element includes a contact lens.

In some embodiments, the optical element includes an intraocular implant.

In another aspect, the invention features a system for providing multi-focal visual correction. The system includes a profile calculation module configured to determine a plurality of visual conditions to which an eye is to be exposed, determine effects of the visual conditions on a pupil of the eye, determine a target wavefront profile on the basis of the effects, and determine a wavefront-correction profile on the basis of the target wavefront profile.

In some embodiments, the system further includes a wavefront mapping module configured to determine a wavefront aberration map for the eye. The profile calculation module is configured to determine the wavefront-correction profile on the basis of the target wavefront profile and the wavefront aberration map.

In some embodiments, determining effects of the visual conditions on a pupil of the eye includes determining a change in a size of a pupil of the eye, or a change in a position of the pupil.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will become apparent from the following description, and from the claims.

DESCRIPTION

Figure 1:
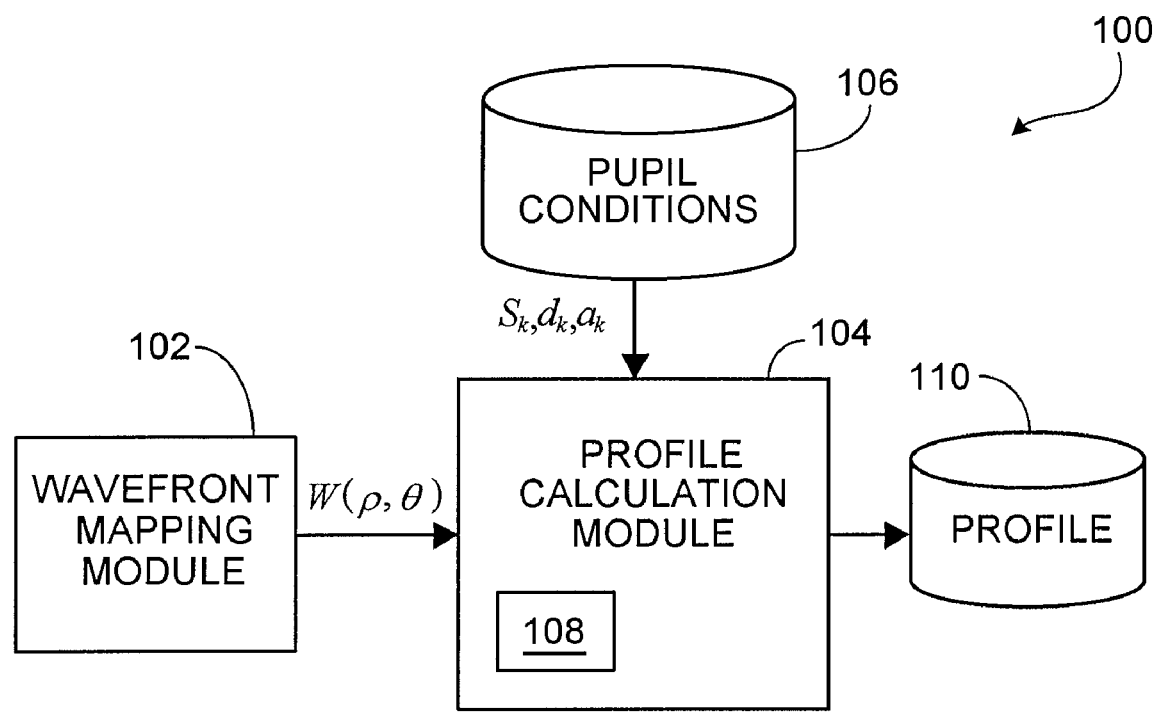
FIG. 1 is a block diagram of an ocular wavefront-correction profiling system.

Referring to FIG. 1, an ocular wavefront-correction profiling system 100 includes a wavefront mapping module 102 that provides a wavefront aberration map of a subject's eye as input to a profile calculation module 104. The profile calculation module 104 also takes pupil conditions 106 as input. The pupil conditions 106 can include, for example, the size (e.g., radius) and position of the pupil relative to the limbus of the eye. Alternatively, the size and position of the pupil can be registered relative to any other remarkable ocular structure or marks. The profile calculation module 104 includes a mode solver 108 to determine a wavefront-correction profile 110 that can be used to perform laser ablation on the cornea to compensate for loss of focusing ability for multiple distances of regard (e.g., a near and a far distance of regard), as described in more detail below. Alternatively, the wavefront-correction profile 110 can be used to shape (e.g., using laser ablation) an optical element including contact lenses or spectacles (e.g., for testing the profile with feedback from the subject before surgery is performed) or an intraocular implant. For example, the wavefront-correction profile 110 can be used to shape a surface of a phakic or pseudophakic intraocular lens before insertion and placement.

Alternatively, in some embodiments, the system 100 can take pupil and wavefront measurements after insertion and placement of an adjustable implant (e.g., a light-adjustable lens (LAL) whose shape changes in response to applied optical radiation, or a nematic liquid-crystal lens whose index of refraction varies in response to an applied electric field). The measurements would subsequently be used to selectively modify optical properties of the adjustable implant (e.g., thickness of a LAL, or index of a nematic liquid crystal lens) according to the wavefront-correction profile 110.

The wavefront mapping module 102 can use any of a variety of techniques for measuring or estimating a wavefront aberration map with respect to a reference surface (e.g., a plane). For example, the wavefront mapping module 102 can use measurement techniques and/or devices such as a spatially resolved refractometer, laser ray tracing, a Tcherning aberroscope, a Shack-Hartmann wavefront sensor, or dynamic skiascopy. The collected wavefront data represents aberrations over an area bounded by the subject's pharmacologically dilated pupil. Alternatively, the wavefront mapping module 102 can estimate wavefront aberrations based on anatomical measurements of a portion of the subject's eye.

For example, a wavefront aberration map can be estimated from a map of corneal topography. Thus, the wavefront aberration map can represent aberrations due to propagation through some or all of the structures in the eye.

The wavefront mapping module 102 provides a mathematical description of the wavefront aberration map to the profile calculation module 104. One convenient mathematical description of the wavefront aberration map is a Zernike spatial mode expansion of the wavefront aberration map $W(\rho,\theta)$ (in polar coordinates):

$$W(\rho, \theta) = \sum_{n=2}^{N} \sum_{\substack{m=-n \\ p(m)=p(n)}}^{n} C_n^m Z_n^m(\rho, \theta)$$

where the $Z_n^m(\rho,\theta)$ are mutually orthogonal Zernike basis functions (or "spatial modes") of radial order n and angular frequency m and $C_n^m$ are the corresponding weighting coefficients. The spatial modes are defined over a unit circle (i.e., $\rho \leq 1$) that corresponds to the pupil over which the wavefront aberrations are defined. The radial order n is summed from 2 to N since the radial orders n=0 and n=1 (corresponding to constant and tilt terms) do not contribute to the aberrations in the wavefront aberration map. The angular frequency m is summed from –n to n, where p(m)=p(n) (i.e., the parity of m is the same as the parity of n). Thus, for an expansion up to the fourth radial order (N=4), the expansion includes the spatial modes: $Z_2^{-2}(\rho,\theta)$, $Z_2^0(\rho,\theta)$, $Z_2^2(\rho,\theta)$, $Z_3^{-3}(\rho,\theta)$, $Z_3^{-1}(\rho,\theta)$, $Z_3^1(\rho,\theta)$, $Z_3^3(\rho,\theta)$, $Z_4^{-4}(\rho,\theta)$, $Z_4^{-2}(\rho,\theta)$, $Z_4^0(\rho,\theta)$, $Z_4^2(\rho,\theta)$, and $Z_4^4(\rho,\theta)$. The spatial modes, when normalized to have zero mean and unit variance over the unit circle, are given by:

$$Z_n^m(\rho, \theta) = \begin{cases} \sqrt{2(n+1)}\, R_n^{|m|}(\rho)\cos(|m|\theta), & \text{if } m > 0 \\ \sqrt{2(n+1)}\, R_n^{|m|}(\rho)\sin(|m|\theta), & \text{if } m < 0 \\ \sqrt{(n+1)}\, R_n^0(\rho), & \text{if } m = 0 \end{cases}$$

where, $$R_n^{|m|}(\rho) = \sum_{s=0}^{(n-|m|)/2} \frac{(-1)^s (n-s)!}{s![(n+m)/2-s]![(n-m)/2-s]!} \rho^{n-2s}$$

Figure 2A:
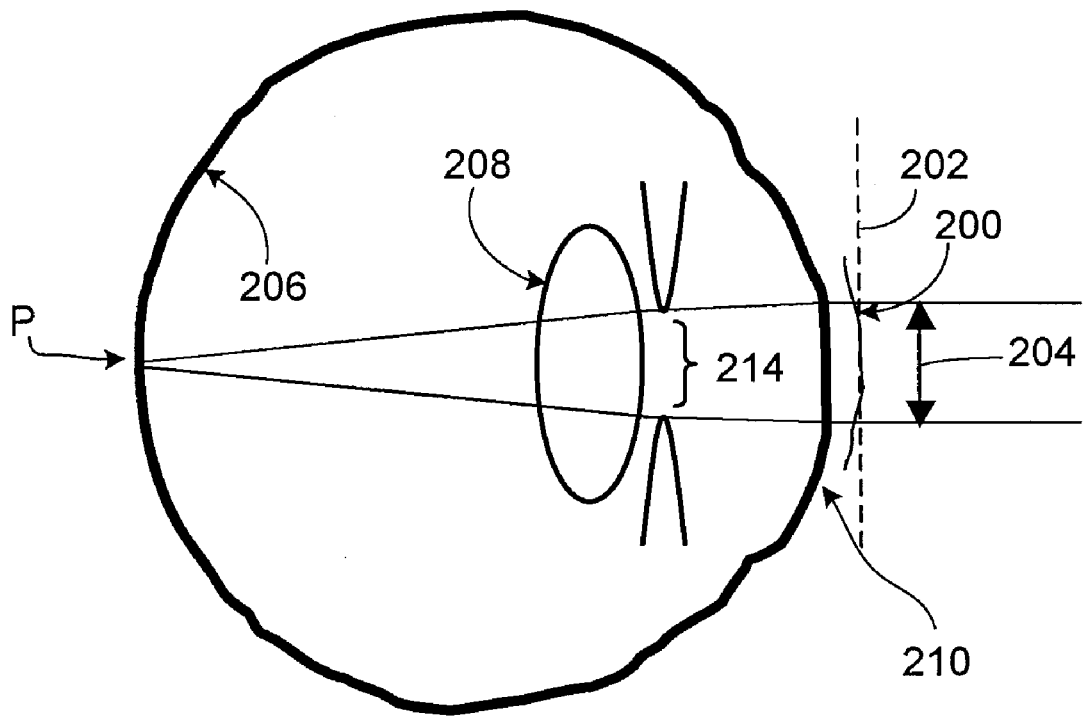
FIG. 2A is a schematic diagram of an eye and a reference plane for wavefront aberrations.
Figure 2B:
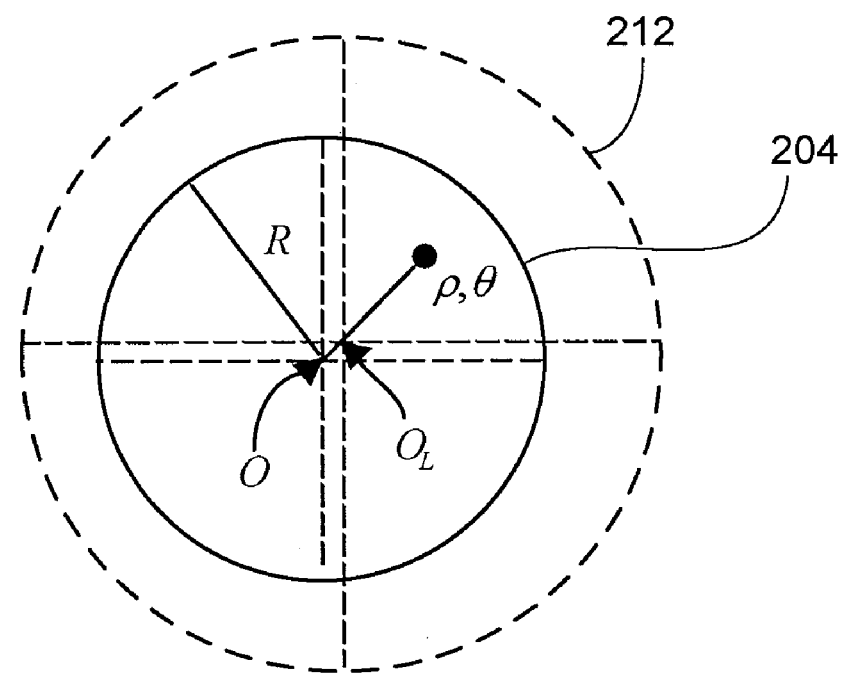
FIG. 2B is a schematic of a coordinate system for a pupil area with respect to the limbus.

Referring to FIGS. 2A and 2B, the wavefront aberration map $W(\rho,\theta)$ represents a deviation of a wavefront 200 from a reference surface 202 over a pupil area 204. The wavefront 200 represents the effects of a spherical wavefront propagating from a point P on the retina 206, through the anatomical structures of the eye (e.g., crystalline lens 208 and cornea 210), to the reference surface 202 just in front of the cornea 210. In this example, the reference surface 202 is flat (i.e., planar) and corresponds to an eye that is fixated on a "far" point (i.e., the farthest possible distance of regard). Alternatively, the reference surface 202 can have other shapes (e.g., spherical) for other assumed states of the eye. If the structures of the eye were "perfect" (i.e., if they caused no aberrations), the wavefront 200 would be flat, and would thus have $W(\rho,\theta)=0$ over the pupil area 204.

The pupil area 204 and its location can be measured for different lighting and fixation (i.e., distance of regard) conditions. The center O of the pupil area 204 is measured relative to the center $O_L$ of the limbus 212. The coordinates of a point $\rho,\theta$ in the aberration map $W(\rho,\theta)=0$ are defined in terms of a polar coordinate system centered at O. The radius R of the pupil area 204 is also measured. The largest size of the pupil area 204 corresponds to a pharmacologically dilated eye.

Since the pupil area 204 is measured from outside the cornea 210, the size of the pupil area 204 may be different from the actual internal size 214 of the pupil.

The pupil conditions 106 for a subject's eye are measured under various lighting and fixation conditions (e.g., using a pupillometer or camera). For example, room lighting is varied from less than 1 lux to 1000 lux while the subject fixates on points at specific distances. The pupil conditions 106 include measurements of pupil size and position for fixation distances and room lighting that correspond to a subject's visual needs and/or desires for "far visual conditions" (e.g., driving at night, watching movies, working outdoors, etc.) and for "near visual conditions" (e.g., reading with bright light, looking at x-rays, playing piano, etc.) for bifocal correction. Pupil conditions for more than two fixation conditions, e.g., for trifocal or multifocal correction, can be included. A pupil condition is measured or estimated based on a desired visual condition (e.g., a far or near visual condition). A desired visual condition can be measured directly or inferred on the basis of measurements indicative of a subject's intent to accommodate for the desired visual condition (e.g., measurement of contraction a subject's ciliary muscle). Such inferred measurements are fully described in U.S. Pat. No. 6,638,304, incorporated herein by reference in its entirety.

Figure 3:
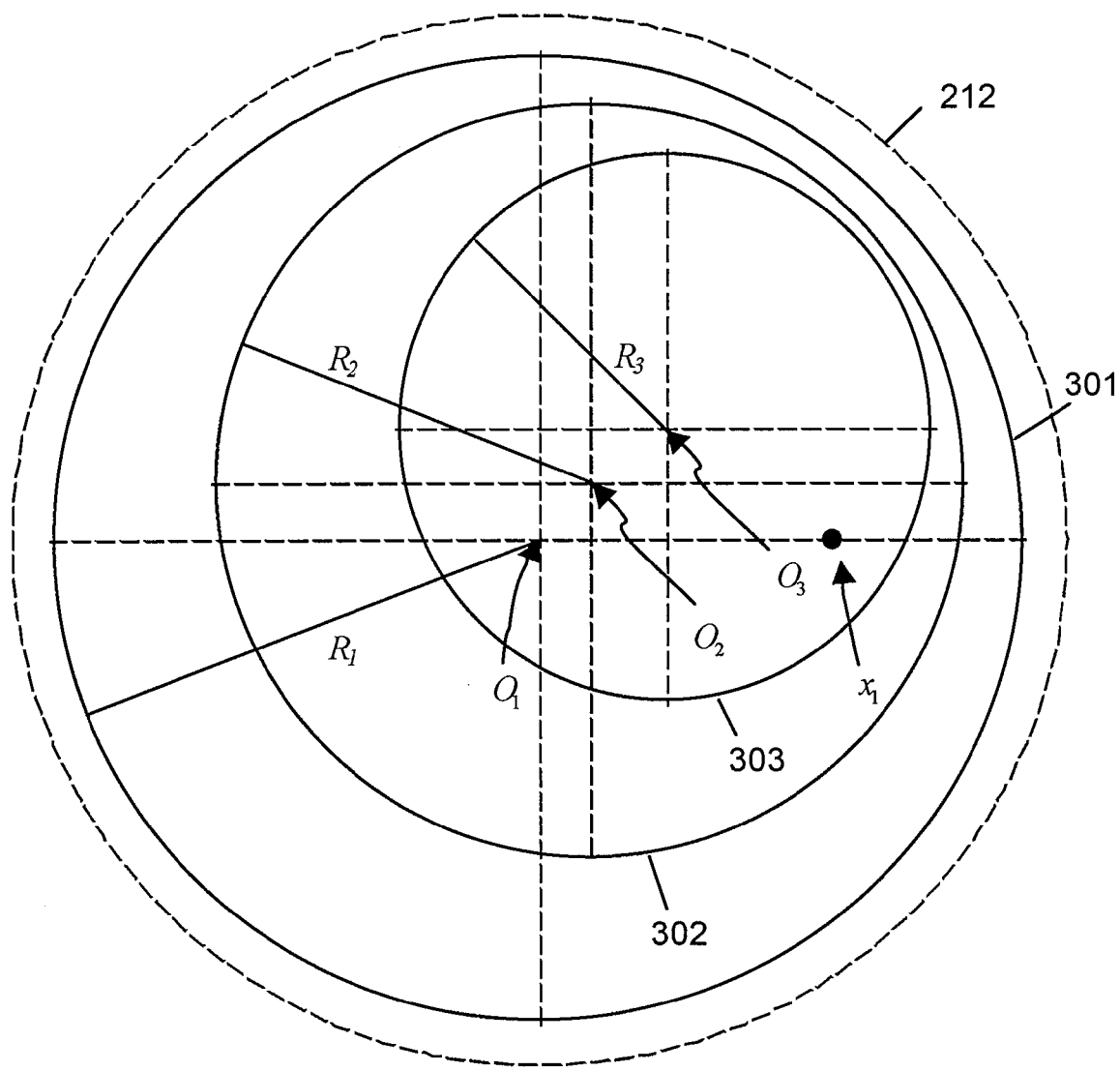
FIG. 3 is a schematic showing three pupil locations.

Referring to FIG. 3, in one embodiment, the pupil conditions 106 include three origin and radius measurements of a subject's pupil relative to the origin $O_L$ of the limbus 210. A first origin $O_1$ and radius $R_1$ correspond to a pharmacologically dilated pupil 301. A second origin $O_2$ and radius $R_2$ correspond to a scotopic (i.e., naturally dilated) pupil 302 while the eye is in a desired far fixation condition. A third origin $O_3$ and radius $R_3$ correspond to a constricted pupil 303 while the eye is in a desired near fixation condition.

The profile calculation module 104 uses relative pupil condition parameters in calculations performed by the mode solver 108. The parameter S represents the relative ratio of pupil sizes: $S_1=1$, $S_2=R_2/R_1$, $S_3=R_3/R_1$. The parameter $d_1$ represents the distance of the shift between pupil conditions: $d_1=0$, $d_2=d(O_1, O_2)$, $d_3=d(O_1, O_3)$, where the function $d(O_1, O_2)$ gives the distance between origins $\vec{O}_1$ and $\vec{O}_2$ normalized by $R_1$. Non-zero values of $d_2$, $d_3$, etc. represent shifting (or "decentration") of the pupil such that the corresponding pupil positions are non-concentric with respect to one another. The parameter a represents the angle from the horizontal of the shift between pupil conditions: $a_2 = \angle(\overrightarrow{O_1 x_1}, \overrightarrow{O_1 O_2})$, $a_3 = \angle(\overrightarrow{O_1 x_1}, \overrightarrow{O_1 O_3})$, where $x_1$ is a point on the x axis of a Cartesian coordinate system centered at $O_1$.

In other embodiments, more or fewer pupil conditions are used. The ratio of pupil sizes can be weighted selectively.

The profile calculation module 104 determines an "add" parameter $\Delta C_2^0$ that corresponds to the amount of focusing power (in Zernike RMS units) needed to supplement a subject's existing accommodation ability so that the subject can focus an image on the retina in the near fixation condition of $\vec{O}_3$. Any of a variety of techniques can be used to estimate $\Delta C_2^0$. For example, a "glass reading test" can be performed on the subject to determine aberrations in an eye as a function of a subject's accommodation. Optionally, other "add" parameters can be estimated to more accurately represent the changes in aberrations between the far and near pupil and fixation conditions, for example, $\Delta C_4^0$, $\Delta C_6^0$, etc. A wavefront aberration map can be obtained through a subject's non-pharmacologically dilated pupil to assist in estimating the add parameters. The change of particular aberrations (such as spherical aberration) as a function of accommodation can be measured from the aberration map and used to determine the corresponding "add" parameter for that particular aberration (e.g., $\Delta C_4^0$ for spherical aberration).

The wavefront mapping module 102 provides "reference coefficients" for the spatial mode expansion of the wavefront aberration map $W(\rho,\theta)$, which is measured through the pupil (of radius $R_1$) of the pharmacologically dilated eye. The coordinates of a point $\Sigma,\theta$ in the aberration map $W(\rho,\theta)$ are defined in terms of a polar coordinate system centered at $\vec{O_1}$. The reference coefficients $C_n^m$ are input into the mode solver 108 along with the relative pupil condition parameters $S_2$, $S_3$, $d_2$, $d_3$, $a_2$, $a_3$, and the add parameter $\Delta C_2^0$.

The mode solver 108 determines a set of "target coefficients" and one or more sets of "modified coefficients." The target coefficients $C_n^m(1)$ correspond to a spatial mode expansion of a target wavefront aberration map representing a desired "target wavefront profile" for optical properties (e.g., surface shape) associated with a subject's vision (e.g., a subject's vision after cornea shaping or after contact lens shaping). The ocular wavefront-correction profiling system 100 generates a wavefront-correction profile 110 based on the difference between the "target wavefront profile" and a "reference wavefront profile" corresponding to the reference coefficients of the subject's pre-operative wavefront profile.

The target coefficients represent solutions satisfying one or more constraints on the modified coefficients. The modified coefficients correspond to a spatial mode expansion of a modified wavefront aberration map due to the effects of constriction of the pupil and decentration of the pupil. In one embodiment, the constraints on two sets of modified coefficients $C_n^m(2)$ and $C_n^m(3)$ include the following constraints on the modified "defocus coefficient" (i.e., coefficient with n=2 and m=0):

$$C_2^0(2)=0$$

$$C_2^0(3)=\Delta C_2^0$$

where $C_2^0(2)$ is a modified defocus coefficient based on the shift in pupil conditions from the pharmacologically dilated pupil 301 to the scotopic pupil 302, and $C_2^0(3)$ is the modified defocus coefficient based on the shift in pupil conditions from the scotopic pupil 302 to the constricted pupil 303.

Other constraints are possible some of which can be expressed as a linear combination of the modified coefficients. For example, the mode solver 108 can include constraints on the relative sizes of different coefficients (e.g., based on empirically derived preferences for some coefficients over others).

Target coefficients are selected based on a value of a metric compared to a threshold. For example, the metric may include the root mean square (RMS) of the target coefficients or the metric may include any quadratic function of the target coefficients. Each target coefficient can be weighted selectively. Initially, all the weights are equal and set to 1. The weights are then varied in the process of computing different candidate solutions.

The modified coefficients $C_n^m(2)$ and $C_n^m(3)$ are calculated as a linear function of the target coefficients $C_n^{m'}(1)$:

$$C_n^m(k) = \sum_{n'=0}^{N} \sum_{\substack{m'=-n' \\ p(m')=p(n')}}^{n'} {}_n^m P_{n'}^{m'} C_{n'}^{m'} \quad (1)$$

The coefficients ${}_n^m P_{n'}^{m'}$ of the four dimensional array P are calculated as integrals over the unit disk, using orthogonality of Zernike polynomials:

$$ {}_n^m P_{n'}^{m'} = \frac{1}{\pi} \int_0^1 \int_{-\pi}^{+\pi} Z_{n'}^{m'} Z_n^m \rho \cdot d\rho \cdot d\theta $$

where $Z_{n'}^{m'}$ is calculated in the polar coordinate system centered at $O_k$.

For example, for an expansion up to N=6, the modified defocus coefficients $C_2^0(2)$ and $C_2^0(3)$ are calculated as follows (with k=2.3 and assuming $R_k < R_1$):

$C_2^0(k) = S_k^2 C_2^0(1)$ $+ 2\sqrt{6} S_k^2 d_k \sin(a_k) C_3^{-1}(1)$ $+ 2\sqrt{6} S_k^2 d_k \cos(a_k) C_3^1(1)$ $+ 2\sqrt{30} S_k^2 d_k^2 \sin(2a_k) C_4^{-2}(1)$ $+ 2\sqrt{15} S_k^2 (S_k^2 - 1 + 4d_k^2) C_4^0(1)$ $+ 2\sqrt{30} S_k^2 d_k^2 \cos(2a_k) C_4^2(1)$ $+ 20 S_k^2 d_k^3 \sin(3a_k) C_5^{-3}(1)$ $+ 6 S_k^2 d_k^3 (5 S_k^2 - 4 + 10 d_k^2) \sin(a_k) C_5^{-1}(1)$ $+ 6 S_k^2 d_k^3 (5 S_k^2 - 4 + 10 d_k^2) \cos(a_k) C_5^1(1)$ $+ 20 S_k^2 d_k^3 \cos(3a_k) C_5^3(1)$ $+ 5\sqrt{42} S_k^2 d_k^2 \sin(4a_k) C_6^{-4}(1)$ $+ 5\sqrt{42} S_k^2 d_k^2 (3 S_k^2 - 2 + {}^4 d_k^2) \sin(2a_k) C_6^{-2}(1)$ $+ 5\sqrt{21} S_k^2 (3 S_k^4 - 5 S_k^2 + 30 S_k^2 d_k^2 + 2 - d_k^4) C_6^0(1)$ $+ 5\sqrt{42} S_k^2 d_k^2 (3 S_k^2 - 2 + 4 d_k^2) \cos(2a_k) C_6^2(1)$ $+ 5\sqrt{42} S_k^2 d_k^2 \cos(4a_k) C_6^4(1)$ where $S_k = R_k/R_1$, $d_k = d(O_1, O_k)$ and $a_k = \angle(\vec{O_1 x_1}, \vec{O_1 O_k})$.

The mode solver 108 selects the target coefficients that yield a metric satisfying a threshold condition. One threshold condition uses the point-spread functions of the modified wavefront aberration maps $W^{(2)}(\rho,\theta)$ and $W^{(3)}(\rho,\theta)$ that correspond to the modified coefficients $C_2^0(2)$ and $C_2^0(3)$, and their respective pupil conditions. For example, a point-spread function PSF is calculated as:

$$ PSF = \left| FT\left\{ A(\rho,\theta) \exp\left( i \frac{2\pi}{\lambda} W(\rho,\theta) \right) \right\} \right|^2 $$

where FT corresponds to a Fourier Transform, $A(\rho,\theta)$ is an aperture function defining the circular pupil area for the given pupil conditions, and $\lambda$ is the wavelength of light used to measure $W(\rho,\theta)$. For the reference coefficients for the spatial mode expansion of the wavefront aberration map $W(\rho,\theta)$ that is measured through the pupil (of radius $R_1$) of the pharmacologically dilated eye, the aperture function is $A(\rho,\theta)=1$ for $\rho \leq 1$, and $A(\rho,\theta)=0$ otherwise. For the modified coefficients, the aperture function is modified according to the corresponding relative pupil constriction and decentration. The threshold condition, for example, can include comparing a value of a "spread metric" based on the point-spread functions for the given pupil conditions to values of the spread metric for a diffraction-limited Airy disk pattern: $|FT\{u(\rho/\rho_0)\}|^2$, where $u(\rho)$ is the unit step function and $\rho_0$ is the relative pupil size for the given pupil conditions (e.g., $\rho_0 = R_2/R_1 = S_1$). One such metric is the second moment of the PSF divided by the second moment of the corresponding Airy disk pattern. For two sets of pupil conditions, the threshold condition may compare the sum or the product of their respective values of the spread metric to a threshold value.

Initially, the mode solver 108 sets the target coefficients to the reference coefficients measured with the pharmacologically dilated pupil 301: $C_n^m(1) = C_n^m$. Then the mode solver 108 searches in some neighborhood around these initial conditions for values of the target coefficients $C_n^m(1)$ that satisfy the constraints for the modified defocus coefficients and minimize the selected error criterion. The mode solver 108 may generate multiple "candidate solutions" (i.e., candidate sets of target coefficients) that satisfy the constraints and yield the same or similar minimized values of the metric. In such cases, the ocular wavefront-correction profiling system 100 can select one or more of the candidate solutions according to the threshold condition. The threshold condition can be based on any of a variety of image plane metrics generated for each of the candidate solutions.

Examples of other metrics that can be used are the Optical Transfer Function (OTF), which is the Fourier Transform of the PSF, the Modulation Transfer Function (MTF), which is the magnitude of the OTF, and the Phase Transfer Function (PTF), which is the phase of the OTF. These metrics can be calculated for each of the pupil conditions and any wavelength. In some embodiments, the MTF for white light is calculated for the different candidate solutions. A final solution can be chosen as the candidate solution that satisfies the constraints and that maximizes the volume under a three-dimensional plot of the MTF for one or both of the largest and the smallest pupil sizes.

Alternatively, the ocular wavefront-correction profiling system 100 can generate multiple wavefront-correction profiles (e.g., 5-10) based on the multiple candidate solutions. Multiple "preview lenses" can be made to allow a subject to test the visual effects of the various profiles (e.g., through visual acuity tests) and to select one to use. For example, the preview lenses can be used in trial frames, held by hand, or used as a contact lens. Alternatively, the multiple candidate solutions can be represented by a deformable mirror array to directly distort the wavefront before transmission to the subject's eye. A subject can view various objects at various pupil sizes and/or illumination conditions through an optical system with deformable mirrors that simulate the candidate solutions. The subject can then choose the best compromise or best solution. These or other techniques can be used to simulate different candidate solutions.

The wavefront-correction profile 110 can optionally account for predicted postoperative biological effects (e.g., wound healing) of a surgical procedure. For wavefront guided laser ablation of the cornea, the profile 110 enables visual correction for multiple pupil and fixation conditions to be performed in only a single surgical procedure. Thus, instead of correcting vision by optimizing accommodation and minimizing higher order aberrations for a single set of pupil and fixation conditions, the ocular wavefront-correction profiling system 100 can produce a profile 110 that incorporates selectively induced aberrations to trade-off correcting vision for multiple sets of pupil and fixation conditions.

FIGS. 4A-4H, 5A-5H, and 6A-6H show results from three exemplary solutions from the mode solver 108. The pupil conditions for these examples were measured from the eye of a 49 year old male subject. The resulting relative pupil condition parameters were $S_2 = 0.589$, $S_3 = 0.405$, $d_2 = 0$, $d_3 = 0.013$, $a_2 = 0$, $a_3 = 0.64$ radians.

The value of a given modified defocus coefficient $C_2^0$ (i) (in microns) can be calculated based on a selected defocus parameter D (in diopters) using the analytical formula:

$$C_2^0(i) = \frac{Dr_i^2}{4\sqrt{3}}$$

where $r_i$ is the radius of the pupil domain associated with the modified defocus coefficient.

For the first exemplary solution, the mode solver 108 used the following constraints on the modified defocus coefficient $C_2^0(2)$ (corresponding to the scotopic pupil 302) and the modified defocus coefficient $C_2^0(3)$ (corresponding to the constricted pupil 303):

$$C_2^0(2) = 0$$

$$C_2^0(3) = \frac{Dr_3^2}{4\sqrt{3}}$$

The three exemplary solutions differ in the radius $r_3$ of the domain chosen for the calculation of the constraint on $C_2^0(3)$. The domain in each example is a circle within the region corresponding to the constricted pupil 303 and centered at $O_3$, but the domain can have a different (e.g., smaller) radius $r_3$ than $R_3$ (i.e., the patient's pupil radius in the desired near fixation condition in the chosen light ambiance). For $r_3 = R_3$, $C_2^0(3) = 0.1664$ microns, and for smaller values of $r_3$, the value of $C_2^0(3)$ is smaller. These variations in the size of the domain $r_3$ used for generating alternative solutions enable trade-off between near and far visual conditions. Using a smaller domain for near vision gives "less weight" to the near vision correction and "more weight" to the far vision correction.

In the illustrated examples, the domains over which near vision is corrected are centered at $O_3$. Alternatively, the domains can be slightly decentered with respect to $O_3$. The MTF and PSF used as metrics for the near vision solutions are calculated considering the full pupil domain of radius $r_3 = R_3$. Any of a variety of optimization strategies are possible. For example, strategy to preserve distance vision in some cases would be to used the S3 diameter without modification, but reduce the value of the C20 on S3 for the optimization.

The MTF is used as a metric for each of the solutions to satisfy a threshold condition for selecting the target coefficients. In this case, the threshold condition corresponds to the area under the MTF curve being larger than a threshold value. The resulting modified wavefront aberration maps $W^{(2)}(\rho,\theta)$ and $W^{(3)}(\rho,\theta)$ that satisfy the above constraints on the modified coefficients $C_2^0(2)$ and $C_2^0(3)$ and have a metric that satisfies the threshold condition are given below. The order of the maps is N=6.

Figure 4A:
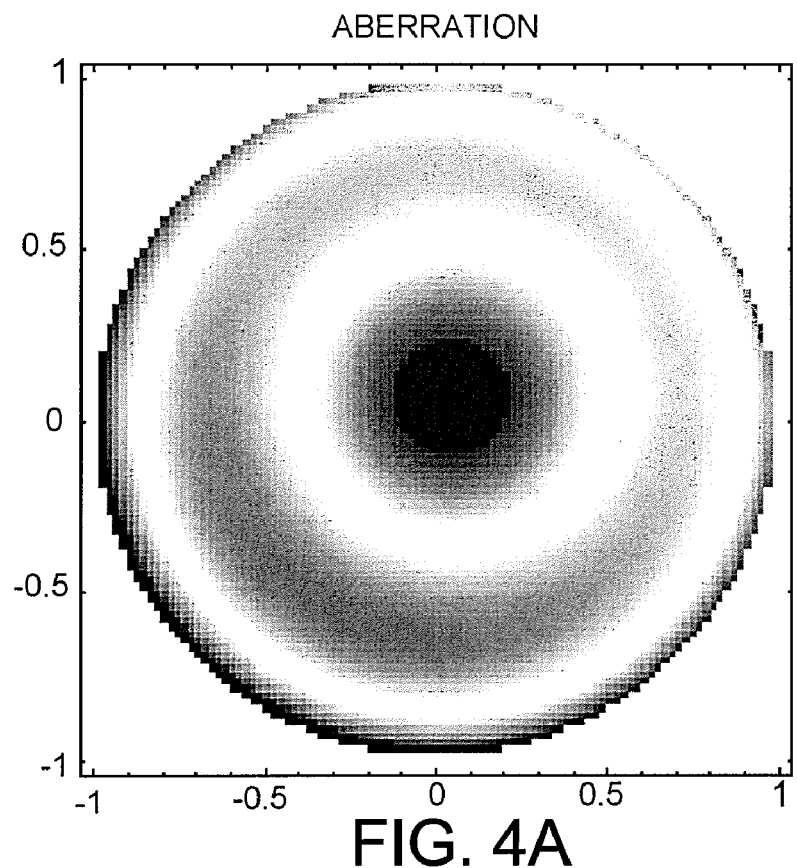
FIGS. 4A/B, 5A/B, and 6A/B are two-dimensional plots of modified wavefront aberration maps.
Figure 4B:
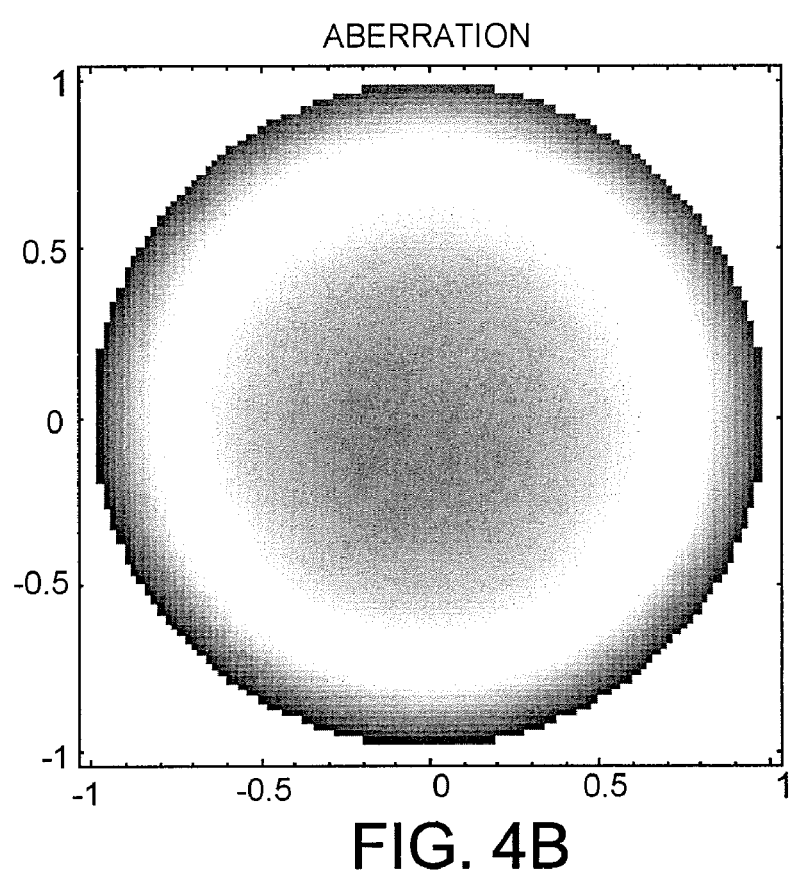
FIGS. 4C/D, 5C/D, and 6C/D are spatial frequency plots of a modular transfer function.
FIGS. 4E/F, 5E/F, and 6E/F are angular plots of a point spread function.
FIGS. 4G/H, 5G/H, and 6G/H are two-dimensional plots of a point spread function.
Figure 4C:
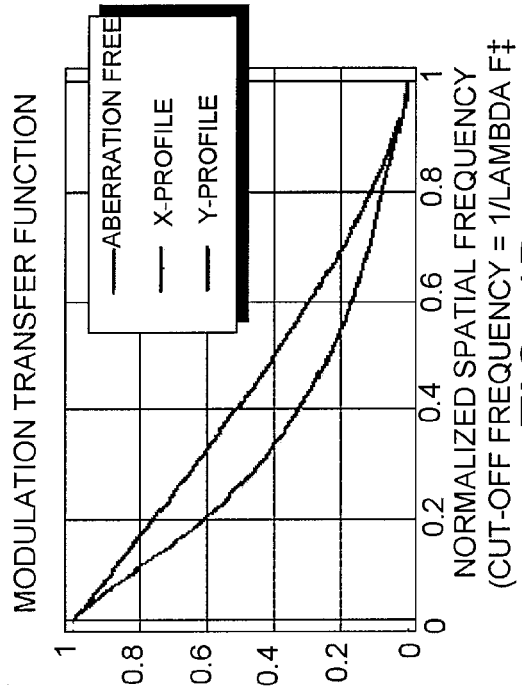
Figure 4D:
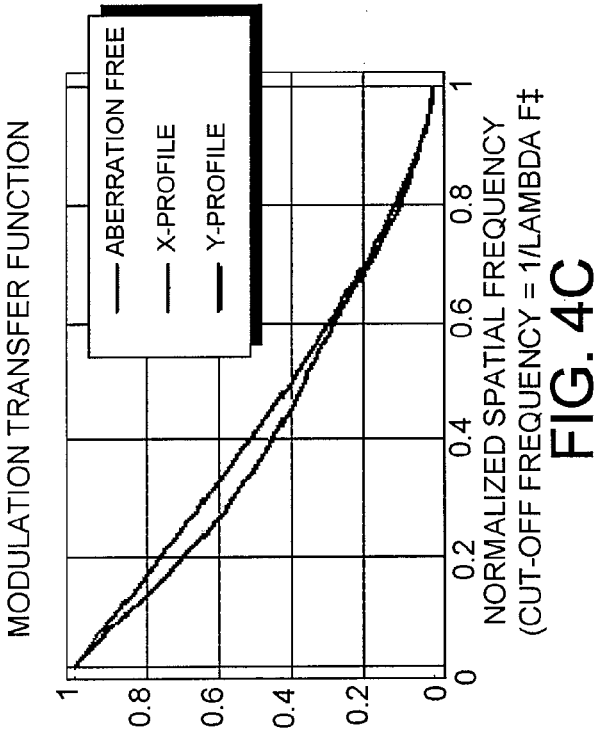
Figure 4E:
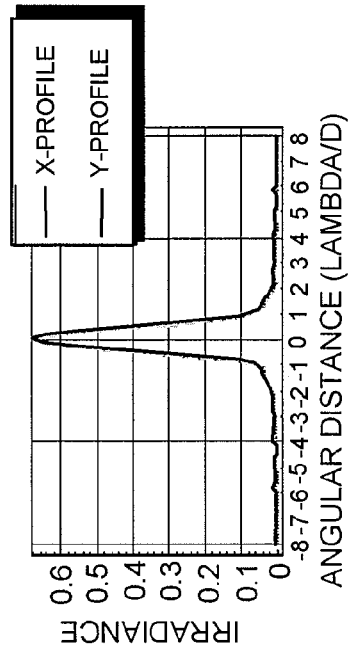
Figure 4F:
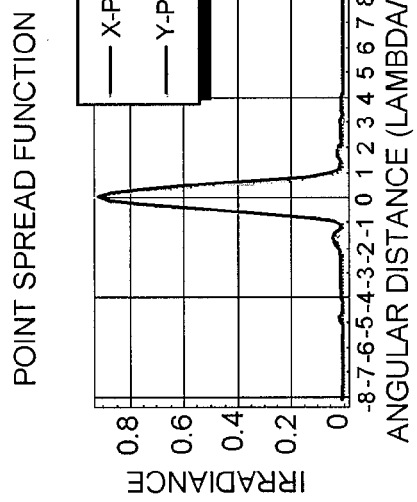
Figure 4G:
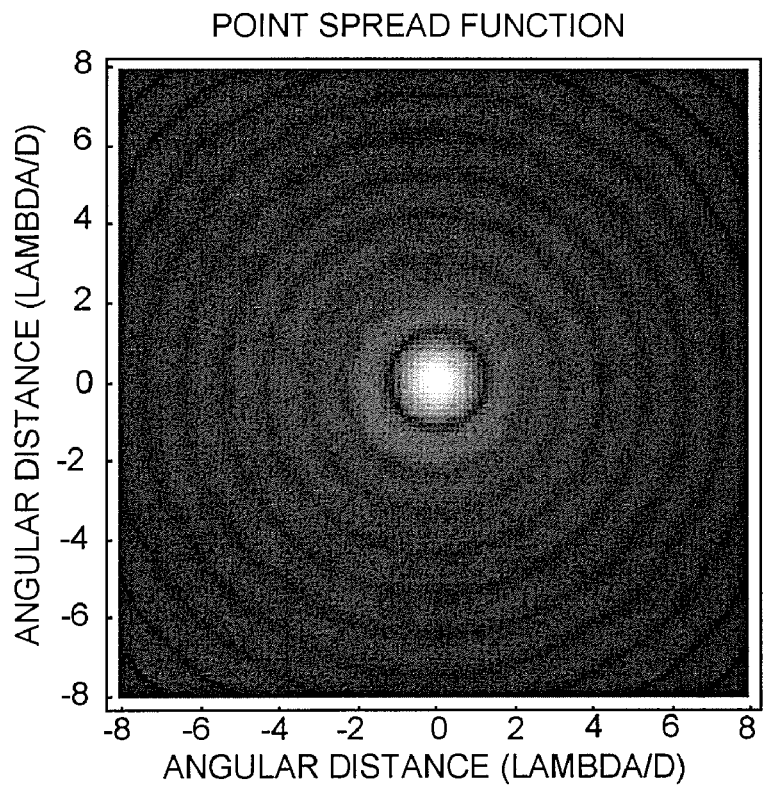
Figure 4H:
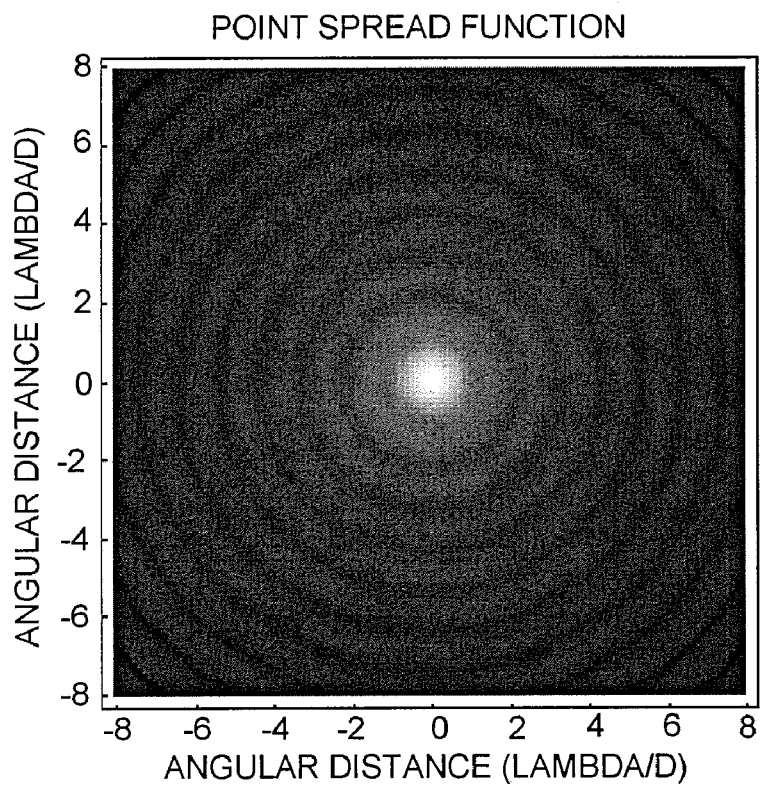

The first exemplary solution yields the following modified wavefront aberration map $W^{(2)}(\rho,\theta)$ for the scotopic pupil 302 (illustrated in FIG. 4A), corresponding to the eye looking at a distant point:

$-0.0994(1-6\rho^2+6\rho^4)+0.01(-1+12\rho^2-30\rho^4+20\rho^6)+$
  $0.0316\rho(-2+3\rho^2)\cos[\Theta]-$ $0.002473\rho(3-12\rho^2+10\rho^4)\cos[\Theta]-0.003748\rho^2\cos$
  $[2\Theta]+0.001135\rho^2(-3+4\rho^2)\cos[2\Theta]-$ $0.000074\rho^2(6-20\rho^2+15\rho^4)\text{Cos}[2\Theta]+0.04252\rho(-2+3\rho^2)\text{Sin}[\Theta]-0.003322\rho(3-12\rho^2+10\rho^4)\text{Sin}[\Theta]-$ $0.001121\rho^2 \text{Sin}[2\Theta]+0.0003398\rho^2(-3+4\rho^2)\text{Sin}[2\Theta]-0.00000223\rho^2(6-20\rho^2+15\rho^4)\text{Sin}[2\Theta]$ and the following wavefront aberration map $W^{(3)}(\rho,\theta)$ for the constricted pupil 303 (illustrated in FIG. 4B), corresponding to the eye looking at a near point (33 cm away):

$-0.17(-1+2\rho^2)0.04061(1-6\rho^2+6\rho^4)+0.00184(-1+12\rho^2-30\rho^4+20\rho^6)+0.0112\rho(-2+3\rho^2)\text{Cos}[\Theta]-$ $0.0002819\rho(3-12\rho^2+10\rho^4)\text{Cos}[\Theta]-0.000918\rho^2 \text{Cos}[2\Theta]+0.000304\rho^2(-3+4\rho^2)\text{Cos}[2\Theta]-$ $0.0000137\rho^2(6-20\rho^2+15\rho^4)\text{Cos}[2\Theta]+0.0000449\rho^3 \text{Cos}[3\Theta]+0.01504\rho(-2+3\rho^2)\text{Sin}[\Theta]-$ $0.000378\rho(3-12\rho^2+10\rho^4)\text{Sin}[\Theta]-0.000274\rho^2 \text{Sin}[2\Theta]+0.00009099\rho^2(-3+4\rho^2)\text{Sin}[2\Theta]-0.00001634\rho^2 \text{Sin}[3\Theta]$ FIGS. 4C and 4D are plots of the MTF versus spatial frequency for the scotopic pupil 302 and the constricted pupil 303, respectively. The MTF has been normalized to a value of 1 at zero spatial frequency. For comparison, the upper curves in FIGS. 4C and 4D represent an aberration free MTF. FIGS. 4E and 4F are angular plots of the PSFs for the scotopic pupil 302 and the constricted pupil 303, respectively. FIGS. 4G and 4H are two-dimensional plots of the same PSFs with the peak intensity (corresponding to white) normalized according to the peak value shown in the corresponding angular plot.

Figure 5A:
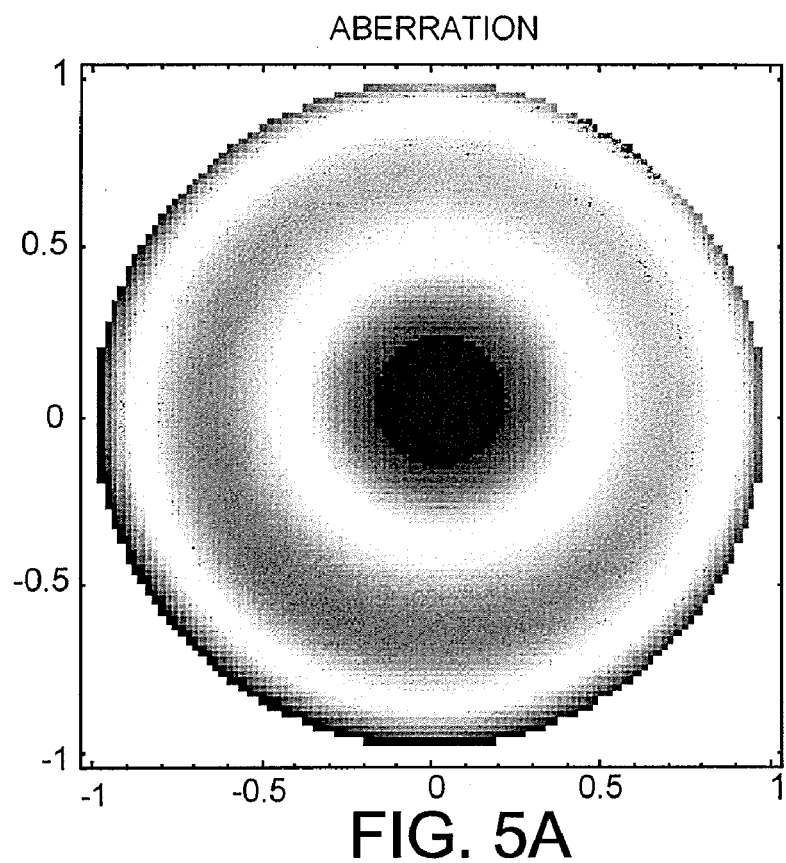
Figure 5B:
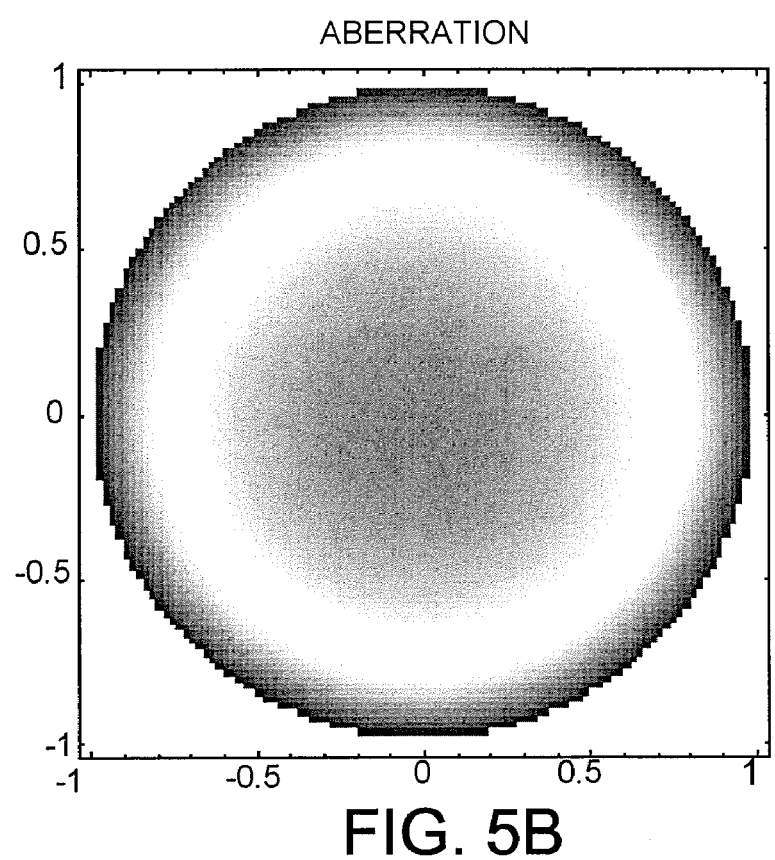
Figure 5C:
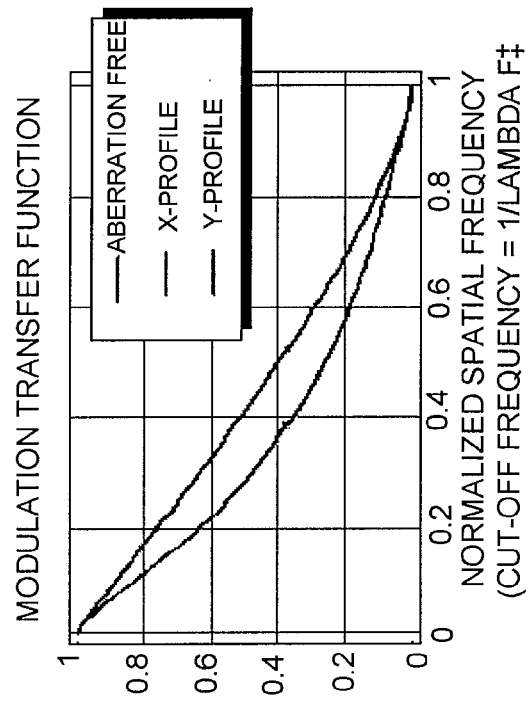
Figure 5D:
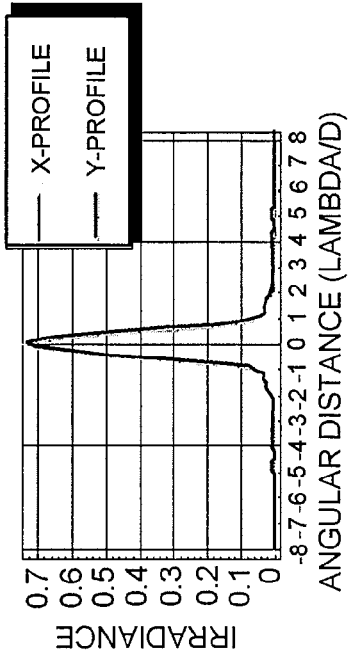
Figure 5E:
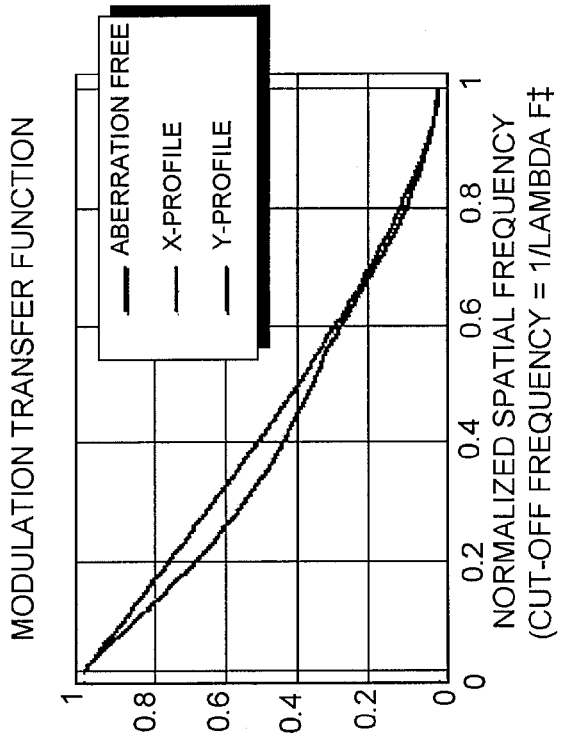
Figure 5F:
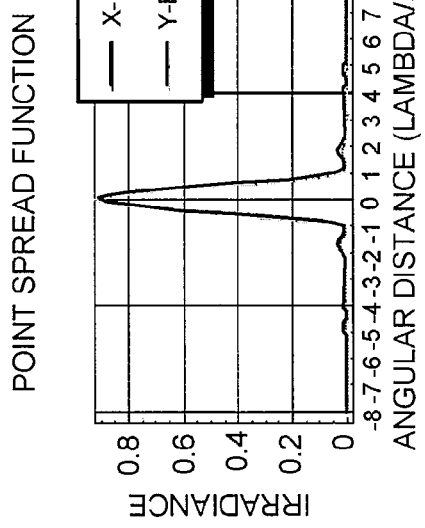
Figure 5G:
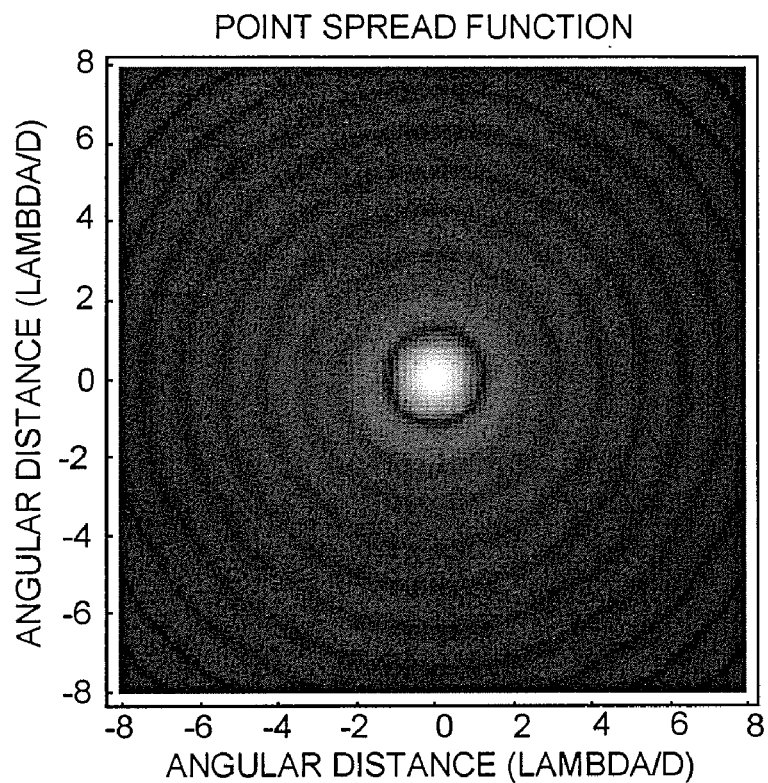
Figure 5H:
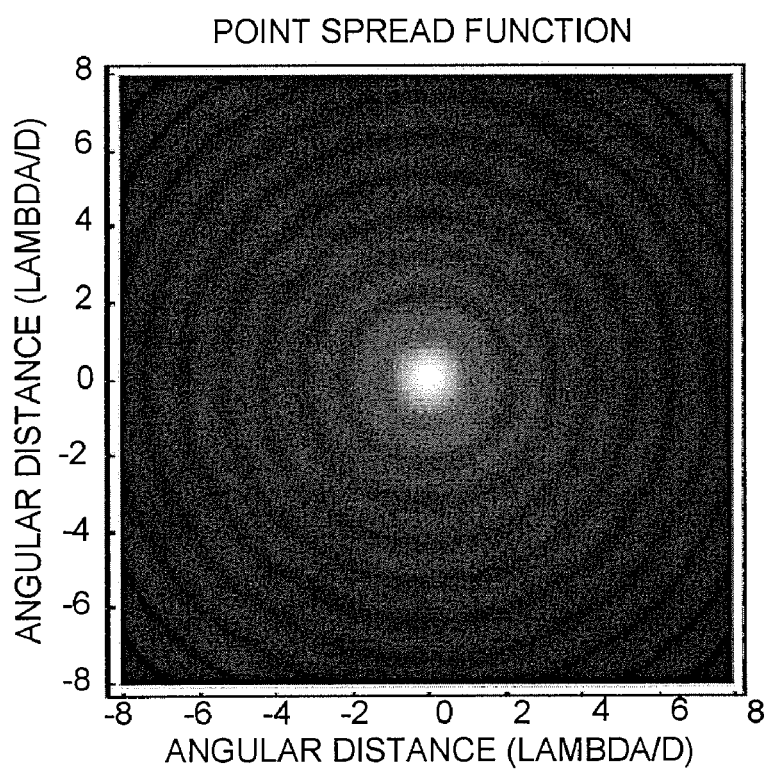

The second exemplary solution yields the following modified wavefront aberration map $W^{(2)}(\rho,\theta)$ for the scotopic pupil 302 (illustrated in FIG. 5A), corresponding to the eye looking at a distant point:

$-0.11(1-6\rho^2+6\rho^4)+0.01485(-1+12\rho^2-30\rho^4+20\rho^6)+0.02256\rho(-2+3\rho^2)\text{Cos}[\Theta]-$ $0.00229\rho(3-12\rho^2+10\rho^4)\text{Cos}[\Theta]-0.000208\rho^2 \text{Cos}[2\Theta]+0.00088\rho^2(-3+4\rho^2)\text{Cos}[2\Theta]-$ $0.000076\rho^2(6-20\rho^2+15\rho^4)\text{Cos}[2\Theta]+0.0308\rho(-2+3\rho^2)\text{Sin}[\Theta]-0.003087\rho(3-12\rho^2+10\rho^4)\text{Sin}[\Theta]-$ $0.0006252\rho^2 \text{Sin}[2\Theta]+0.00026\rho^2(-3+4\rho^2)\text{Sin}[2\Theta]-0.00002278\rho^2(6-20\rho^2+15\rho^4)\text{Sin}[2\Theta]$ and the following wavefront aberration map $W^{(3)}(\rho,\theta)$ for the constricted pupil 303 (illustrated in FIG. 5B), corresponding to the eye looking at a near point (33 cm away):

$-0.1533(-1+2\rho^2)-0.03655(1-6\rho^2+6\rho^4)+0.001569(-1+12\rho^2-30\rho^4+20\rho^6)+0.005081\rho(-2+3\rho^2)\text{Cos}[\Theta]-$ $0.000078\rho(3-12\rho^2+10\rho^4)\text{Cos}[\Theta]-0.000658\rho^2 \text{Cos}[2\Theta]+0.0001899\rho^2(-3+4\rho^2)\text{Cos}[2\Theta]+0.00002\rho^3 \text{Cos}[3\Theta]+$ $0.006825\rho(-2+3\rho^2)\text{Sin}[\Theta]-0.00010559\rho(3-12\rho^2+10\rho^4)\text{Sin}[\Theta]-0.0001972\rho^2 \text{Sin}[2\Theta]+0.00005684\rho^2(-3+4\rho^2)\text{Sin}[2\Theta]$ FIGS. 5C and 5D are plots of the MTF versus spatial frequency for the scotopic pupil 302 and the constricted pupil 303, respectively. The MTF has been normalized to a value of 1 at zero spatial frequency. For comparison, the upper curves in FIGS. 5C and 5D represent an aberration free MTF. FIGS. 5E and 5F are angular plots of the PSFs for the scotopic pupil 302 and the constricted pupil 303, respectively. FIGS. 5G and 5H are two-dimensional plots of the same PSFs with the peak intensity (corresponding to white) normalized according to the peak value shown in the corresponding angular plot.

Figure 6A:
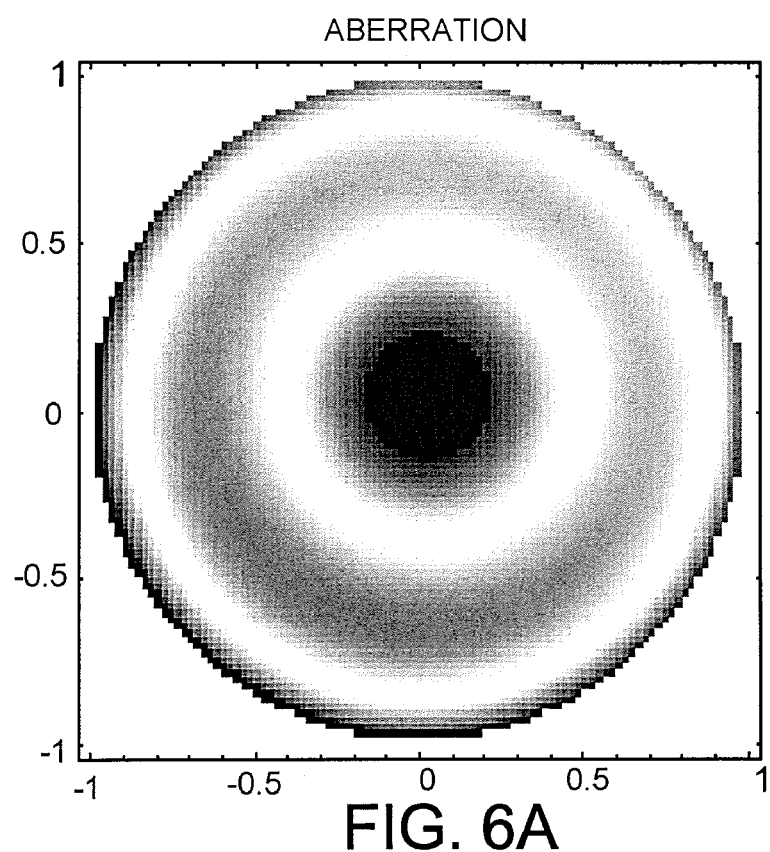
Figure 6B:
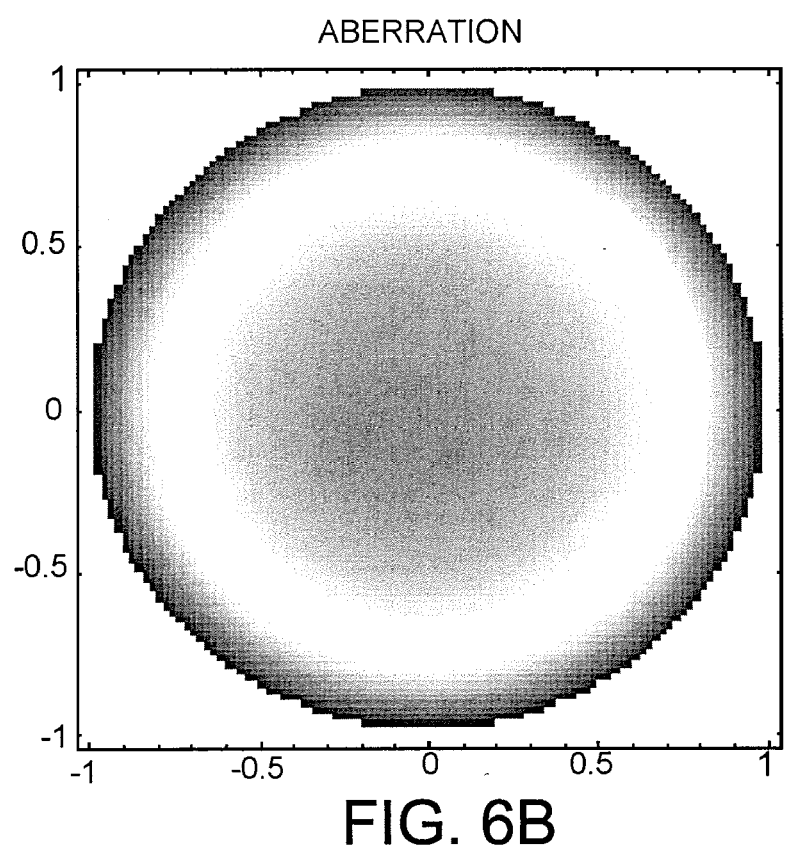
Figure 6C:
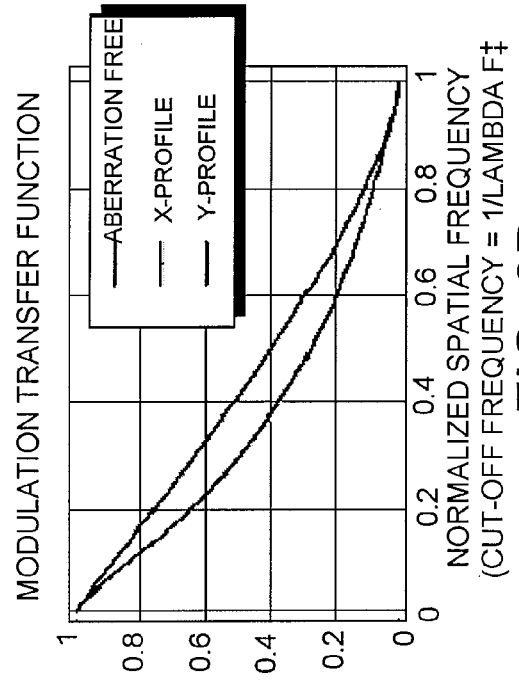
Figure 6D:
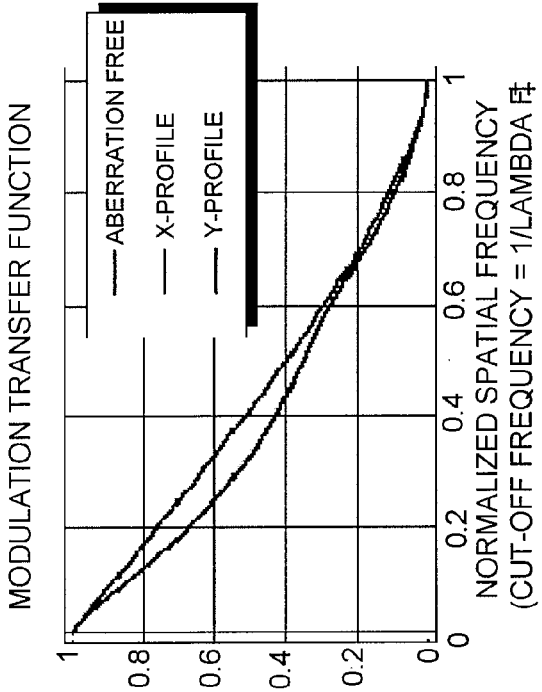
Figure 6E:
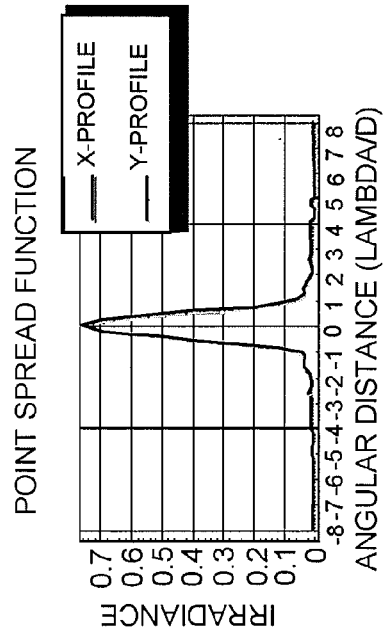
Figure 6F:
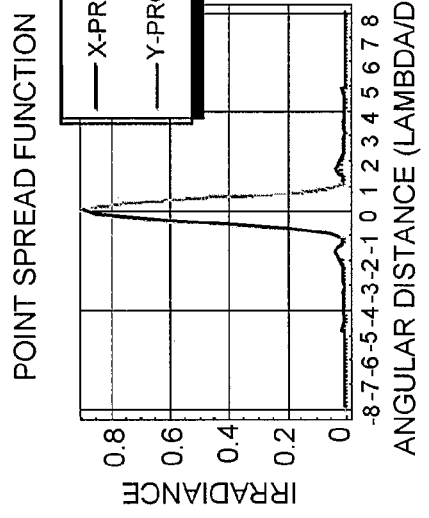
Figure 6G:
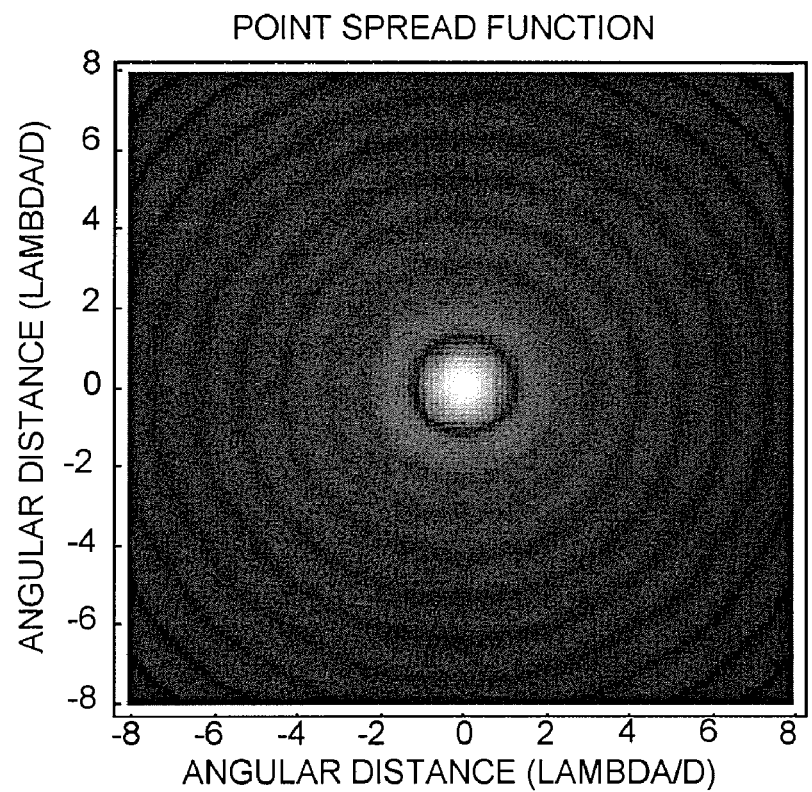
Figure 6H:
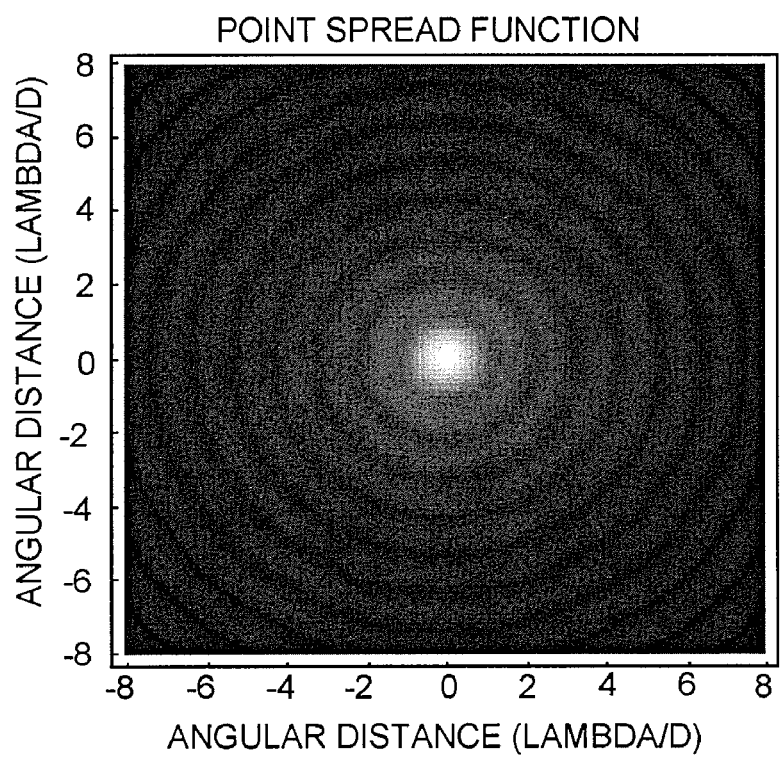

The third exemplary solution yields the following modified wavefront aberration map $W^{(2)}(\rho,\theta)$ for the scotopic pupil 302 (illustrated in FIG. 6A), corresponding to the eye looking at a distant point:

$-0.12064(1-6\rho^2+6\rho^4)+0.0153(-1+12\rho^2-30\rho^4+20\rho^6)+0.02384\rho(-2+3\rho^2(\text{Cos}[\Theta]-$ $0.00242\rho(3-12\rho^2+10\rho^4)\text{Cos}[\Theta]-0.0022053\rho^2 \text{Cos}[2\Theta]+0.000933\rho^2(-3+4\rho^2)\text{Cos}[2\Theta]-$ $0.000802\rho^2(6-20\rho^215\rho^4)\text{Cos}[2\Theta]+0.032028\rho(-2+3\rho^2)\text{Sin}[\Theta]-0.00326\rho(3-12\rho^210\rho^4)\text{Sin}[\Theta]-$ $0.00066002\rho^2 \text{Sin}[2\Theta]+0.000279\rho^2(-3+4\rho^2)\text{Sin}[2\Theta]-0.00024\rho^2(6-20\rho^2+15\rho^4)\text{Sin}[2\Theta]$ and the following wavefront aberration map $W^{(3)}(\rho, \Theta)$ for the constricted pupil 303 (illustrated in FIG. 6B), corresponding to the eye looking at a near point (33 cm away):

$-0.144(-1+2\rho^2)-0.03776(1-6\rho^2+6\rho^4)+0.0016211(-1+12\rho^2-30\rho^4+20\rho^6)+0.005469\rho(-2+3\rho^2)\text{Cos}[\Theta]-$ $0.000894\rho(3-12\rho^210\rho^4)\text{Cos}[\Theta]-0.0006849\rho^2 \text{Cos}[2\Theta]+0.000199\rho^2(-3+4\rho^2)\text{Cos}[2\Theta]+$ $0.007346\rho(-2+3\rho^2)\text{Sin}[\Theta]-0.0001201\rho(3-12\rho^2+10\rho^4)\text{Sin}[\Theta]-0.000205\rho^2 \text{Sin}[2\Theta]+0.0000596\rho^2(-3+4\rho^2)\text{Sin}[2\Theta]$ FIGS. 6C and 6D are plots of the MTF versus spatial frequency for the scotopic pupil 302 and the constricted pupil 303, respectively. The MTF has been normalized to a value of 1 at zero spatial frequency. For comparison, the upper curves in FIGS. 6C and 6D represent an aberration free MTF. FIGS. 6E and 6F are angular plots of the PSFs for the scotopic pupil 302 and the constricted pupil 303, respectively. FIGS. 6G and 6H are two-dimensional plots of the same PSFs with the peak intensity (corresponding to white) normalized according to the peak value shown in the corresponding angular plot.

It is to be understood that while the invention has been described in conjunction with the detailed description thereof, the foregoing description is intended to illustrate and not limit the scope of the invention, which is defined by the scope of the appended claims.

What is claimed is:

1. A method for providing multi-focal visual correction, the method comprising:
    determining a plurality of visual conditions to which an eye is to be exposed;
    determining effects of the visual conditions on a pupil of the eye including effects on a position of the pupil;
    determining effects of the visual conditions on accommodation by the eye; and
    determining a target wavefront profile on the basis of the effects of the visual conditions on the pupil of the eye and the effects of the visual conditions on accommodation by the eye;
    wherein determining effects of the visual conditions on a pupil of the eye comprises determining a change in a size of the pupil and a change in a position of the pupil.

2. The method of claim 1, wherein:
    determining effects of the visual conditions on a pupil of the eye includes determining a plurality of pupil conditions for the eye, wherein a pupil position corresponding to a first pupil condition is non-concentric with a pupil position corresponding to a second pupil condition; and
    determining a target wavefront profile on the basis of the effects of the visual conditions on the pupil of the eye and the effects of the visual conditions on accommodation by the eye includes determining the target wavefront profile on the basis of the plurality of pupil conditions;

wherein determining a plurality of pupil conditions for an eye comprises determining a change in a size of a pupil of the eye and a change in a position of the pupil.

3. The method of claim 2, wherein determining the change in the position of the pupil comprises determining a distance of a shift between pupil conditions and determining an angle of the shift between the pupil conditions.

4. The method of claim 2, wherein determining a plurality of pupil conditions for an eye comprises determining a plurality of desired visual conditions; and estimating pupil conditions corresponding to each of the plurality of desired visual conditions.

5. The method of claim 2, wherein determining a plurality of pupil conditions for an eye comprises simulating a plurality of desired visual conditions; and measuring pupil conditions resulting from each of the desired visual conditions.

6. The method of claim 2, wherein determining a plurality of pupil conditions for an eye comprises determining a pupil condition corresponding to a lighting condition.

7. The method of claim 6, wherein determining the pupil condition further comprises determining the pupil condition corresponding to a distance of regard.

8. The method of claim 6, wherein determining a plurality of pupil conditions for an eye comprises determining a plurality of pupil conditions corresponding to different lighting conditions varied over the range of approximately 1 lux to 1000 lux.

9. The method of claim 2, wherein determining a plurality of pupil conditions for an eye comprises determining a pupil condition corresponding to a wavelength of light.

10. The method of claim 2, wherein determining a plurality of pupil conditions for an eye comprises recording a pupil condition in an image.

11. The method of claim 2, wherein determining a target wavefront profile comprises selecting a plurality of distances to objects of regard and determining the target wavefront profile at least in part on the basis of the plurality of distances.

12. The method of claim 11, wherein the first pupil condition corresponds to a near distance, and the second pupil condition corresponds to a far distance.

13. The method of claim 12, wherein the plurality of pupil conditions includes a third pupil condition that corresponds to a distance between the near and far distances.

14. The method of claim 2, wherein determining a target wavefront profile comprises inferring desired visual conditions on the basis of measurements indicative of a subject's intent to accommodate for the desired visual conditions.

15. The method of claim 2, wherein determining a plurality of pupil conditions for an eye comprises determining a pupil condition relative to an anatomical reference of the eye.

16. The method of claim 15, wherein determining the pupil condition relative to the anatomical reference of the eye comprises determining a pupil size and a pupil position relative to the anatomical reference of the eye.

17. The method of claim 2, wherein the plurality of pupil conditions comprises at least three pupil conditions.

18. The method of claim 17, wherein the at least three pupil conditions include: a first pupil condition that comprises a first origin corresponding to a position of the center of the pupil and a first size corresponding to the radius of the pupil while the eye is pharmacologically dilated, a second pupil condition that comprises a second origin corresponding to a position of the center of the pupil and a second size corresponding to the radius of the pupil while the eye is naturally dilated and in a far fixation condition, and a third pupil condition that comprises a third origin corresponding to a position of the center of the pupil and a third size corresponding to the radius of the pupil while the eye is constricted and in a near fixation condition.

19. The method of claim 2, wherein a first pupil condition is determined relative to a second pupil condition.

20. The method of claim 1, further comprising:
determining a wavefront aberration map for the eye; and
determining a wavefront-correction profile on the basis of the target wavefront profile and the wavefront aberration map.

21. The method of claim 20, further comprising:
determining the wavefront-correction profile at least in part on the basis of a metric selected from the group consisting of a point spread function, an optical transfer function, a modular transfer function, and a phase transfer function.

22. The method of claim 20, further comprising:
performing laser ablation on the cornea of the eye according to the wavefront-correction profile.

23. The method of claim 20, further comprising:
performing laser ablation a contact lens according to the wavefront-correction profile.

24. The method of claim 1, wherein determining the change in the position of the pupil comprises determining a distance of a shift between visual conditions and determining an angle of the shift between the visual conditions.

25. The method of claim 1, wherein determining effects of the visual conditions on a pupil of the eye comprises estimating pupil conditions corresponding to each of the plurality of visual conditions.

26. The method of claim 1, wherein determining a plurality of visual conditions comprises simulating a plurality of desired visual conditions; and determining effects of the visual conditions on a pupil of the eye comprises measuring pupil conditions resulting from each of the desired visual conditions.

27. The method of claim 1, wherein determining effects of the visual conditions on a pupil of the eye comprises determining a pupil condition corresponding to a lighting condition.

28. The method of claim 27, determining effects of the visual conditions on a pupil of the eye comprises determining a plurality of pupil conditions corresponding to different lighting conditions varied over the range of approximately 1 lux to 1000 lux.

29. A system for providing multi-focal visual correction, the system comprising:
a profile calculation module configured to
determine a plurality of pupil conditions for an eye, wherein a pupil position corresponding to a first pupil condition is non-concentric with a pupil position corresponding to a second pupil condition;
determine a target wavefront profile on the basis of the plurality of pupil conditions; and
determine a wavefront-correction profile on the basis of the target wavefront profile;
wherein determining a plurality of pupil conditions for an eye comprises determining a change in a size of a pupil of the eye and a change in a position of the pupil.

30. The system of claim 29, further comprising:
a wavefront mapping module configured to determine a wavefront aberration map for the eye;

wherein the profile calculation module is configured to determine the wavefront-correction profile on the basis of the target wavefront profile and the wavefront aberration map.

31. A system for providing multi-focal visual correction, the system comprising:

a profile calculation module configured to determine a plurality of visual conditions to which an eye is to be exposed;

determine effects of the visual conditions on a pupil of the eye including effects on a position of the pupil;

determine a target wavefront profile on the basis of the effects; and determine a wavefront-correction profile on the basis of the target wavefront profile;

wherein determining effects of the visual conditions on a pupil of the eye comprises determining a change in a size of the pupil and a change in a position of the pupil.

32. The system of claim 31, wherein determining the change in the position of the pupil comprises determining a distance of a shift between visual conditions and determining an angle of the shift between the visual conditions.

* * * * *